United States Patent
Curran et al.

(10) Patent No.: US 10,081,808 B2
(45) Date of Patent: *Sep. 25, 2018

(54) BIOMOLECULE ISOLATION

(71) Applicant: GenCell Biosystems Ltd., Raheen, County Limerick (IE)

(72) Inventors: Kieran Curran, Ballyclough (IE); David McGuire, Enniscorthy (IE)

(73) Assignee: GENCELL BIOSYSTEMS LTD, Raheen, County Limerick (IE)

( * ) Notice: Subject to any disclaimer, the term of this patent is extended or adjusted under 35 U.S.C. 154(b) by 0 days.

This patent is subject to a terminal disclaimer.

(21) Appl. No.: 15/667,568

(22) Filed: Aug. 2, 2017

(65) Prior Publication Data

US 2018/0016573 A1 Jan. 18, 2018

Related U.S. Application Data

(62) Division of application No. 14/374,727, filed as application No. PCT/IB2013/000478 on Jan. 25, 2013, now Pat. No. 9,777,269.

(60) Provisional application No. 61/590,499, filed on Jan. 25, 2012.

(51) Int. Cl.
| | | |
|---|---|---|
| *G01N 35/00* | (2006.01) | |
| *C12N 15/10* | (2006.01) | |
| *B01F 13/00* | (2006.01) | |
| *B01L 3/00* | (2006.01) | |
| *G01N 35/08* | (2006.01) | |

(52) U.S. Cl.
CPC ...... *C12N 15/1093* (2013.01); *B01F 13/0071* (2013.01); *B01L 3/502761* (2013.01); *B01L 3/502784* (2013.01); *C12N 15/1013* (2013.01); *G01N 35/08* (2013.01); *B01L 2200/0668* (2013.01); *B01L 2300/0838* (2013.01); *B01L 2300/0877* (2013.01); *B01L 2400/043* (2013.01); *B01L 2400/0487* (2013.01); *G01N 35/0098* (2013.01)

(58) Field of Classification Search
None
See application file for complete search history.

(56) References Cited

U.S. PATENT DOCUMENTS

| | | |
|---|---|---|
| 4,141,687 A | 2/1979 | Forrest et al. |
| 5,505,877 A | 4/1996 | Krivohlavek |
| 5,980,936 A | 11/1999 | Krafft et al. |
| 7,129,091 B2 | 10/2006 | Ismagilov et al. |
| 7,138,233 B2 | 11/2006 | Griffiths et al. |
| 7,244,567 B2 | 7/2007 | Chen et al. |

(Continued)

FOREIGN PATENT DOCUMENTS

| | | |
|---|---|---|
| DE | 10111520 A1 | 1/2003 |
| EP | 1019496 B1 | 7/2000 |

(Continued)

OTHER PUBLICATIONS

Kim et al. "Automated Digital Microfluidic Sample Preparation for Next-Generation DNA Sequencing," Journal of Laboratory Automation, vol. 16, No. 6, Dec. 1, 2011, pp. 405-414.

(Continued)

*Primary Examiner* — Rebecca L Martinez
(74) *Attorney, Agent, or Firm* — Bret E. Field; Bozicevic, Field & Francis LLP

(57) ABSTRACT

Methods, devices and systems for handling sample liquids, encapsulating liquids and magnetic particles are disclosed.

20 Claims, 10 Drawing Sheets

(56) References Cited

U.S. PATENT DOCUMENTS

| | | |
|---|---|---|
| 7,252,943 B2 | 8/2007 | Griffiths et al. |
| 7,323,305 B2 | 1/2008 | Leamon et al. |
| 7,439,014 B2 | 10/2008 | Pamula et al. |
| 7,582,446 B2 | 9/2009 | Griffiths et al. |
| 7,638,276 B2 | 12/2009 | Griffiths et al. |
| 7,776,927 B2 | 8/2010 | Chu et al. |
| 7,842,457 B2 | 11/2010 | Berka et al. |
| 7,901,939 B2 | 3/2011 | Ismagliov et al. |
| 7,915,013 B2 | 3/2011 | Cho et al. |
| 7,943,348 B2 | 5/2011 | Cho et al. |
| 8,093,064 B2 | 1/2012 | Shah et al. |
| 8,158,359 B2 | 4/2012 | Leamon et al. |
| 8,273,573 B2 | 9/2012 | Ismagilov et al. |
| 8,304,193 B2 | 11/2012 | Ismagilov et al. |
| 8,329,407 B2 | 12/2012 | Ismagilov et al. |
| 8,367,326 B2 | 2/2013 | Griffiths et al. |
| 8,613,889 B2 | 12/2013 | Pollack et al. |
| 8,637,317 B2 | 1/2014 | Pamula et al. |
| 8,637,324 B2 | 1/2014 | Pollack et al. |
| 8,685,754 B2 | 4/2014 | Pollack et al. |
| 8,709,762 B2 | 4/2014 | Hindson |
| 8,748,102 B2 | 6/2014 | Berka et al. |
| 8,765,380 B2 | 7/2014 | Berka et al. |
| 8,790,876 B2 | 7/2014 | Leamon et al. |
| 9,194,772 B2 | 11/2015 | Lee et al. |
| 2008/0124726 A1 | 5/2008 | Monforte |
| 2008/0226500 A1 | 9/2008 | Shikida et al. |
| 2009/0023189 A1 | 1/2009 | Lau et al. |
| 2009/0131543 A1 | 5/2009 | Weitz et al. |
| 2009/0191594 A1 | 7/2009 | Ohashi |
| 2010/0022414 A1 | 1/2010 | Link et al. |
| 2010/0105112 A1 | 4/2010 | Holtze et al. |
| 2010/0184020 A1 | 7/2010 | Beer |
| 2010/0227323 A1 | 9/2010 | Baeumner et al. |
| 2011/0104816 A1 | 5/2011 | Pollack et al. |
| 2012/0208241 A1 | 8/2012 | Link |
| 2013/0043150 A1 | 2/2013 | Ohashi |
| 2013/0096035 A1 | 4/2013 | Wang et al. |
| 2013/0109575 A1 | 5/2013 | Kleinschmidt et al. |
| 2013/0190189 A1 | 7/2013 | Griffiths et al. |
| 2014/0057363 A9 | 2/2014 | Sista et al. |
| 2014/0069812 A1 | 3/2014 | Pollack et al. |
| 2014/0113300 A1 | 4/2014 | Samuels |
| 2014/0162885 A1 | 6/2014 | Berka et al. |
| 2014/0193807 A1 | 7/2014 | Pamula et al. |
| 2014/0199730 A1 | 7/2014 | Agresti et al. |
| 2014/0199731 A1 | 7/2014 | Agresti et al. |

FOREIGN PATENT DOCUMENTS

| | | |
|---|---|---|
| EP | 1053784 A2 | 11/2000 |
| EP | 0892035 B1 | 10/2004 |
| EP | 1485204 B1 | 2/2006 |
| EP | 1496120 B1 | 3/2007 |
| EP | 1482036 B1 | 10/2007 |
| EP | 1508044 B1 | 9/2010 |
| EP | 1801214 B1 | 11/2010 |
| EP | 2278337 A2 | 1/2011 |
| EP | 2248578 B1 | 6/2012 |
| EP | 1908832 B1 | 12/2012 |
| EP | 2258846 A2 | 12/2012 |
| EP | 2703497 A1 | 3/2014 |
| JP | 60-122374 A | 6/1985 |
| JP | 2006-10332 A | 1/2006 |
| JP | 2011-232260 A | 11/2011 |
| WO | WO 93/03151 A1 | 2/1993 |
| WO | WO 2004/038363 A2 | 5/2004 |
| WO | WO 2005/002730 A1 | 1/2005 |
| WO | WO 2007/024778 A2 | 3/2007 |
| WO | WO 2007/024798 A2 | 3/2007 |
| WO | WO 2007/024800 A2 | 3/2007 |
| WO | WO 2007/024914 A2 | 3/2007 |
| WO | WO 2008/144288 A1 | 11/2008 |
| WO | WO 2009/061372 A1 | 5/2009 |
| WO | WO 2010/104604 A1 | 9/2010 |
| WO | WO 2010/121307 A1 | 10/2010 |
| WO | WO 2012/011091 A2 | 1/2012 |
| WO | WO 2013/111016 A2 | 8/2013 |
| WO | WO 2013/192351 A1 | 12/2013 |
| WO | WO 2014/039587 A1 | 3/2014 |
| WO | WO 2014/083435 A2 | 6/2014 |
| WO | WO 2014/093714 A1 | 6/2014 |
| WO | WO 2014/188281 A2 | 11/2014 |
| WO | WO 2014/207577 A2 | 12/2014 |
| WO | WO 2015/075560 A2 | 5/2015 |
| WO | WO 2015/075563 A2 | 5/2015 |
| WO | WO 2015/120398 A2 | 8/2015 |

OTHER PUBLICATIONS

Lee et al. "On-Chip Procedures for Magnetic Particle-Based Assay in Droplets," 16th International Conference on Miniaturized Systems for Chemistry and Life Sciences, Oct. 28-Nov. 1, 2012, Okinawa, Japan, pp. 347-349.

Lehmann et al. "A Lab-on-a-Chip using magnetic droplets," NSTI—Nanotech 2006, vol. 2, 2006, pp. 477-480.

Mastrobattista et al. "High-throughput screening of enzyme libraries: in vitro evolution of a beta-galactosidase by fluorescence-activated sorting of double emulsions," Chemistry & Biology, vol. 12, Dec. 2005, pp. 1291-1300.

Shen et al. "Application of Magnetic Control Techique in Microfluidic Chips", Progress in Chemistry, vol. 22, No. 1, Jan. 2010, pp. 133-139. (English Abstract Only).

Tawfik et al. "Man-made cell-like compartments for molecular evolution," Nature Biotechnology, vol. 16, Jul. 1998, pp. 652-656.

Utada et al. "Monodisperse Double Emulsions Generated from a Microcapillary Device", Science, vol. 308, Apr. 22, 2005, pp. 537-541.

Wu et al. "A double-emulsion microfluidic platform for in vitro green fluorescent protein expression," Journal of Micromechanics and Microengineering, 21 (2011), 054032, 7 pages.

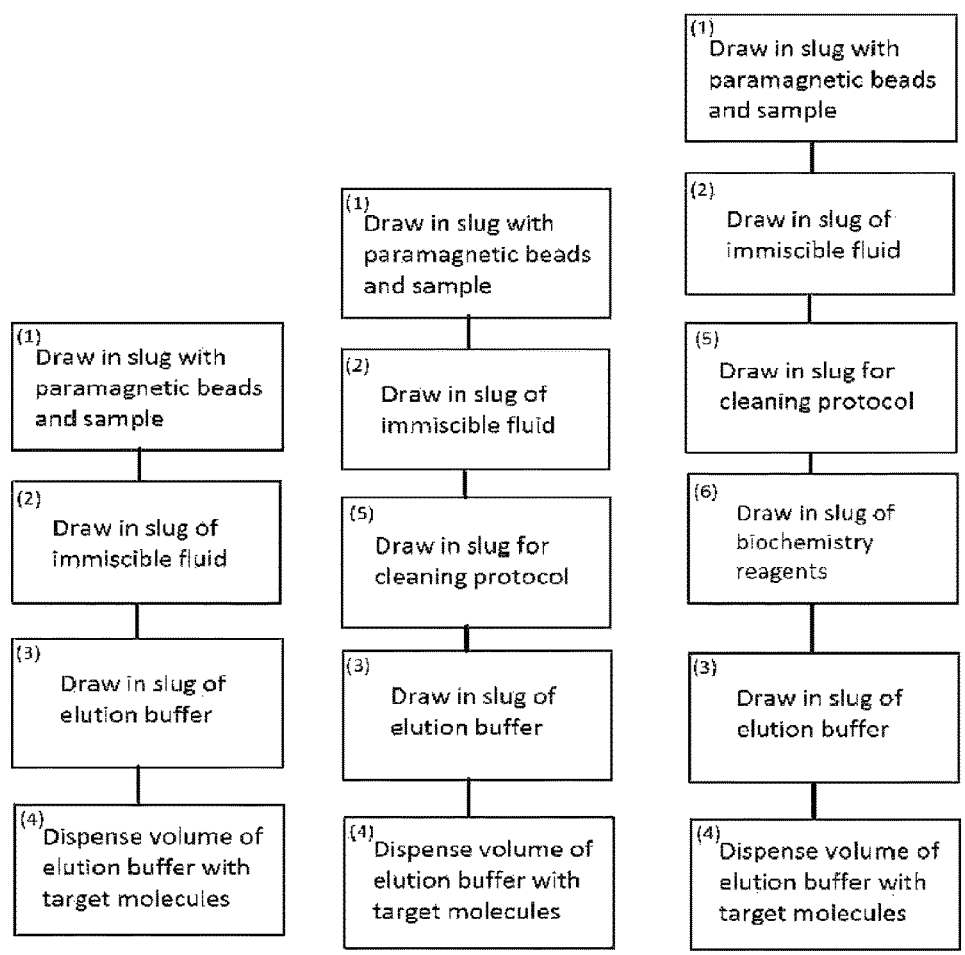

BIOMOLECULE ISOLATION

RELATED APPLICATIONS

This application is a divisional of U.S. application Ser. No. 14/374,727, filed Jul. 25, 2014, which application is a 371 national phase filing of International Application No. PCT/IB2013/000478, filed Jan. 25, 2013, which application claims the benefit of U.S. Provisional Application Ser. No. 61/590,499, filed Jan. 25, 2012, which applications are hereby incorporated herein by reference in their entirety.

BACKGROUND

The isolation of biomolecules is a critical part of any sample processing system. With the development of automated molecular analysis systems the biggest restriction is now in the preparation of the sample and the purification of the target sample.

For all biochemistry processes the isolation and purification of the sample target is critical to its success. The limitations in biochemistry analysis process—pyro-sequencing, nucleic acid ligation, polymerase chain reaction, digital PCR, qPCR, nucleic acid sequencing, protein detection/protein enrichment, genetic bead coating, rare cell detection and cell enrichment—and not limited to these, are due to the starting concentrations of the target and the level of biochemical inhibitors present within the reaction sample used in the analysis.

For most biochemistry analysis a series of pre-analysis steps are performed on the sample to isolate the target from the initial sample and remove biochemistry inhibitors. These steps are typically labour intensive and ultimately reduce the starting concentrations of the target.

The current preferred method of sample purification makes use of spin columns. However spin columns require a number of centrifugation steps and hence cannot be integrated with an automated DNA library preparation platform. Similarly, a purification technique for nucleic acid fragment purification from agarose gels also requires centrifugation steps to achieve the nucleic acid isolation.

One technique used for sample purification is paramagnetic bead-based purification. This method offers an approach that can provide improved DNA recovery rates and tuneable buffer conditions that can be used to selectively bind specific DNA fragment sizes.

The paramagnetic bead based purification is a static well batch process. The current method involves the pipetting of the bead-mixture—paramagnetic beads and a buffer—into a well of a microtitre plate along with the initial sample. The solution is pipetted, mixed, and incubated at room temperature to allow the DNA to bind to the beads. The microtitre plate is then placed onto a magnetic plate. The beads holding the bound DNA move to the edge of the plate and are held by the magnet. Next the supernatant (containing waste) is removed using a pipette and discarded. Following this a number of wash steps are then performed to remove residual waste present on/at the bead pellet. Ethanol is pipetted to the plate containing the bead pellet, incubated and then removed using a pipette. This wash step is repeated twice. An elution buffer is then added. The plate is removed from the magnetic plate and the elution buffer is mixed via pipette mixing. The microtitre plate is placed back onto the magnetic plate. The eluent containing the purified DNA is then withdrawn using a pipette.

The paramagnetic bead based protocol is a labour intensive process and is not easily automated due to the large number of pipetting steps required. The high numbers of pipetting steps also result in large initial and final sample volumes, resulting in high reagent costs per data point.

One application and not limited to this application is for improved sample purification for next generation sequencing platforms. Many next generation sequencing platforms require DNA libraries made up of DNA fragments within a specific range of base pair lengths. In addition, these DNA fragments need to be tagged with specific nucleotide sequences (adapters) to allow the sequences to be amplified using PCR and to allow the library fragments to anneal to the sequencer flow cell. Sequence specific indices can also be added to the DNA fragments to identify individual samples when multiplexing sample within a single flow cell. The tagmentation of DNA (DNA is fragmented and tagged with adapters) and the addition of common adapters and indices are achieved in two separate biological reactions. Following these reactions, the DNA library is cleaned to remove excess nucleotides, enzymes, primers, salts and other contaminants. Consequently, the workflow required to tagment DNA, purify tagmented DNA, add common adapters and indices and purify the final library product is complex and labour intensive.

The systems and methods outlined herein can help achieve sample handling that is contamination-free, low-volume, high-throughput, low-cost, and/or high in sample concentration.

SUMMARY

Devices, systems and methods for using paramagnetic beads for biomolecule isolation and processing.

BRIEF DESCRIPTION OF THE DRAWINGS

FIG. 4 illustrates a method that can be implemented as controller programming.

FIG. 5 illustrates a method that can be implemented as controller programming.

FIG. 6 illustrates a method that can be implemented as controller programming.

DETAILED DESCRIPTION

This disclosure provides in some embodiments systems and methods for the isolation of biomolecules within a conduit. The conduit can have flow in either direction and is controlled by a controller.

Figure 1A:
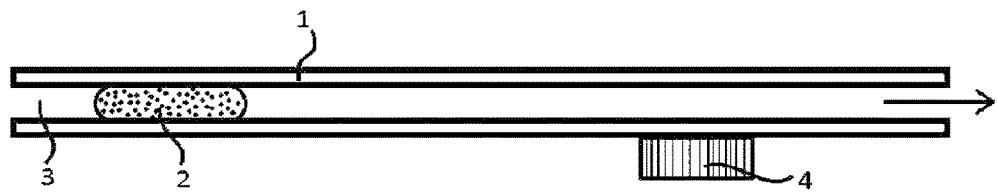
FIG. 1A-1E is a diagram illustrating the continuous flow capillary-based purification system.
Figure 1B:
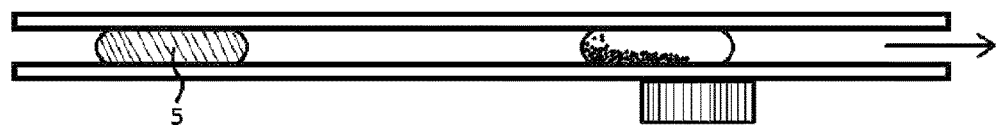
Figure 1C:
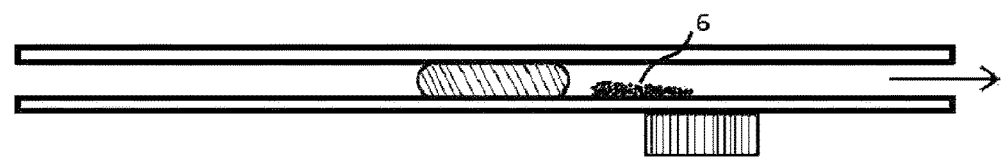
Figure 1D:
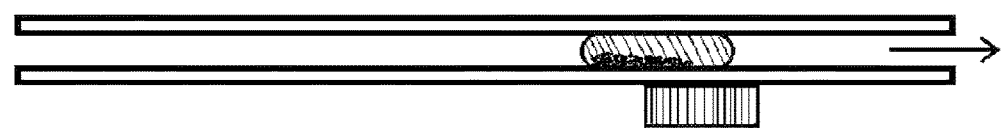
Figure 1E:
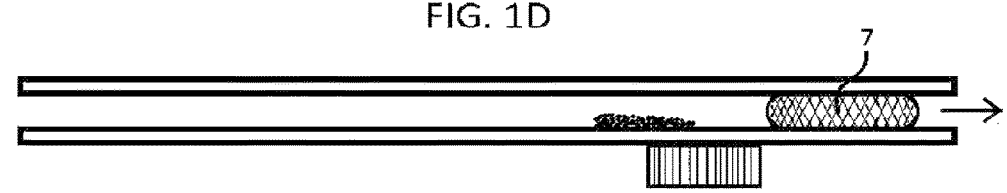

In one embodiment, referring to FIG. 1A, a slug containing paramagnetic beads and sample 2 and immiscible fluid buffer 3 flow within a conduit 1. The sample can include target biomolecules, biochemistry process inhibitors and contaminants. The conduit has at one location along the length a source to generate a magnetic field 4. Referring to FIG. 1B the paramagnetic beads and sample slug 2 and elution buffer slug 5 are separated by an immiscible fluid 3. The paramagnetic beads and sample slug 2 arrives at the magnetic field source 4 where upon the beads are captured within the magnetic field. Referring to FIG. 1C the paramagnetic beads and sample slug 2 continues to flow within conduit 1 while the paramagnetic beads with bound target biomolecules 6 remain captured by the magnetic field source. Referring to FIG. 1D the elution buffer 5 arrives at the magnetic field source and envelopes the captured paramagnetic beads. The bound target biomolecules are released into the elution buffer as it flows along the conduit 1. Referring to FIG. 1E the elution buffer and target biomolecules 7 continue within the conduit 1 for dispensing or further analysis.

Figure 2A:
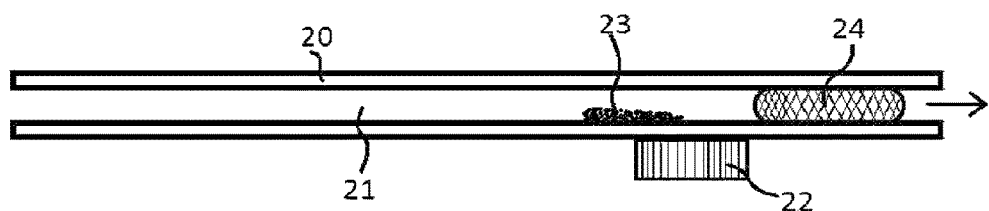
FIG. 2A-2C is a diagram illustrating the bi-directional flow capillary-based purification system.
Figure 2B:
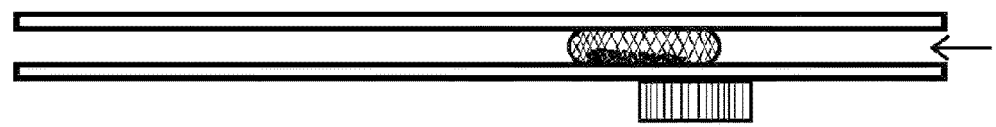
Figure 2C:
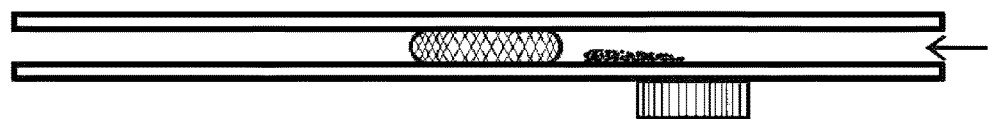

In one embodiment, referring to FIG. 2A following the unbinding of the target biomolecules in the elution buffer 24 form the paramagnetic beads 23 at the magnetic field source 22 in the conduit 20 the flow is reversed. Referring to FIG. 2C the elution buffer and target biomolecules return in the flow over the captured paramagnetic beads 23 by the magnetic field source 22 to return to the original aspiration location for dispensing.

Figure 3A:
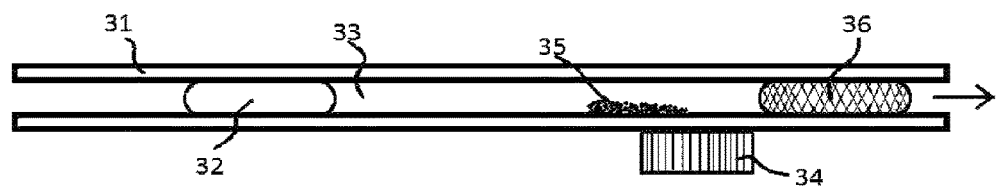
FIG. 3A-3D is a diagram illustrating the magnetic cleanup steps for the continuous flow capillary-based purification system.
Figure 3B:
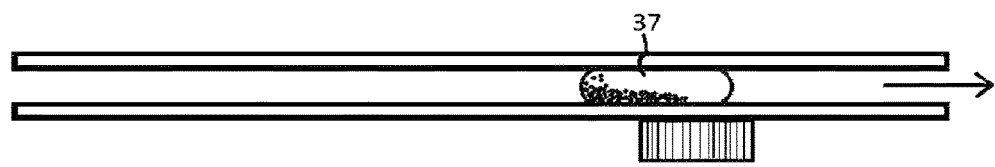
Figure 3C:
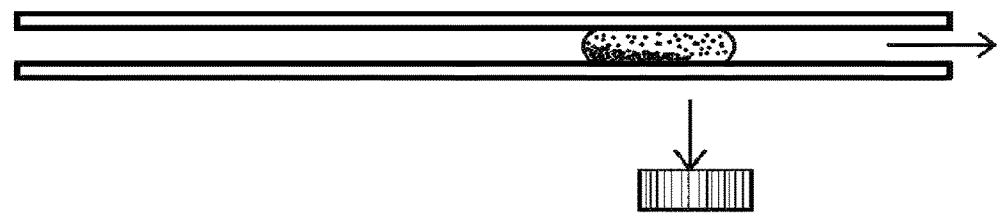
Figure 3D:
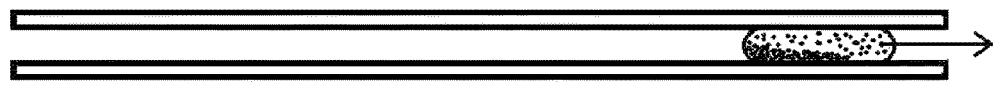

In one embodiment, referring to FIG. 3A, following the unbinding of the target biomolecules in the elution buffer 36 from the paramagnetic beads 35 captured by the magnetic field source 34 in the conduit 31, the immiscible fluid 33 is followed by a bead removal and cleaning slug 32. Referring to FIG. 3B as the bead removal and cleaning slug 32 envelopes the paramagnetic beads 35 the magnetic field source 34 is removed (physically or changed to an off state). Referring to FIG. 3C the paramagnetic beads 35 are responded into the removal and cleaning slug 32 and continue to flow along conduit 31 as slug 37. This bead removal and cleaning process allows for the reuse of the conduit 31 and prevents any cross over contamination of samples.

In one embodiment, the method comprises of the use of a capillary tube, a pump and a localised magnet field at a location along the length of the capillary tube. First a slug of a bead-mixture, which includes a buffer and beads with a biochemistry coating, and the target biomolecule is drawn into the capillary tube. The beads may be magnetic beads with a biochemistry coating or non-magnetic beads (silica, ceramic, a polymer, etc.) with a paramagnetic coating. This is followed by a slug of immiscible fluid, e.g. air or oil and then followed by discreet slugs of ethanol, air, oil and elution buffer. The slugs flow within the tube passing the localised magnetic field, where upon the paramagnetic beads are trapped within the magnetic field, while the other components of the bead-mixture slug continue to flow along the tube, removing all the unbound molecules from the paramagnetic beads. The continuous flow of slugs next brings an oil or air slug, which is used as a buffer to prevent mixing of the bead-mixture slug with the ethanol slug. The ethanol slug cleans any remaining contaminants from the paramagnetic beads. This cleaning step may be repeated depending on the protocol of initial slug pickup sequence. After the ethanol slug has passed an oil buffer passes prior to the slug of elution buffer to prevent any trace elements of ethanol along the tube from mixing with the elution buffer slug. The elution buffer then flows over the paramagnetic beads, releasing the biomolecule targets from the paramagnetic beads into the elution buffer slug. The slug continues to flow along the tube for further biological processing and analysis.

In one embodiment, following the passing of the elution buffer slug over the paramagnetic beads, the flow direction is reversed, and the elution buffer with target biomolecules is dispensed from the system.

In one embodiment, following the passing of the elution buffer slug, the magnetic field is removed and a following slug of ethanol returns the paramagnetic beads to the flow within the capillary tube. This slug is then followed by an oil slug, an ethanol slug, and an oil slug to clean the capillary tube and prevent any contamination of the next slug reactions.

In one embodiment, ethanol slugs are always followed by air slugs; this helps ensure the removal of any ethanol within the system. The air slug allows for the evaporation of ethanol into the air.

Examples of biomolecules include (and are not limited to) cells, nucleic acids, proteins, enzymes, blood, saliva, and organic material.

The bead-mix is typically made up of beads in a buffer solution that includes polyethylene glycol (PEG) and salts.

The bead size is typically within the range of 0.1 to 500 microns.

The beads are magnetic or have a magnetic coating applied.

The bead material can be a polymer, ceramic or metal with a magnetic coating applied.

In one embodiment the beads are functionalised for cell attachment.

In one embodiment the beads are functionalised for nucleic acid attachment.

In one embodiment the beads are functionalised for or limited to the attachment of enzymes, reagents, primers or organic material.

The oils used for generating immiscible phases can include and are not limited to silicone oil, perfluorocarbon oil, and perfluoropolyether oil.

The elution buffers can include and not limited too; sterile water; sterile water with added pH buffers to maintain a pH within a desired range depending on the applications.

The conduit can be a capillary tube.

The conduit material can be a polymer, ceramic or metal.

The conduit may have a hydrophobic surface.

The conduit may be a polymer capillary tube, such as a PTFE material capillary tube.

The conduit diameter is typically within a range of from 10 microns to 10 millimeters in diameter.

In one embodiment the conduit has a wall thickness of at least 10 microns or more.

The internal shape of the conduit can be (and is not necessarily limited to) a profile which is round, square, oval, rectangular, have a wavy surface, have at least one flat surface, or have surface enhancement features.

The flow rate within the conduit is typically within the range of 0.000014/hour to 1000 mL/min.

The external shape of the conduit can be (and is not necessarily limited to) a profile which is round, square, oval, rectangular, have a wavy surface, have at least one flat surface, or have surface enhancement features.

In one embodiment the conduit is a channel etched on a substrate.

In one embodiment the conduit is a channel moulded on a chip.

In one embodiment the conduit is integrated in a chip based analysis system.

At least one or more magnetic fields are located along the length of the conduit. The magnetic field can be generated by a permanent magnet or by some electromagnetic method.

In one embodiment the magnetic fields are controllable, they can be deactivated by either the movement/removal of the magnet or the de-energising/neutralisation of the electromagnetic field.

In one embodiment the magnetic field sources are arranged circumferentially around the conduit generating multiple poles.

In one embodiment the magnetic field sources are arranged along the conduit length to generate multiple poles.

In one embodiment the flow through the system is generated by positive pressure.

In one embodiment the flow through the system is generated by negative pressure.

In one embodiment, the method comprises of the use of a capillary tube, a pump and a localised magnet field at a location along the length of the capillary tube. First a slug of a bead-mixture (buffer and beads with a biochemistry coating) is drawn into the capillary tube. This is followed by a slug of immiscible fluid, e.g. air or oil and then followed by a slug of the sample for purification. Following this a further immiscible slug is drawn up and further discreet slugs of ethanol, air, oil and elution buffer. The slugs flow within the tube passing the localised magnetic field, whereupon the paramagnetic beads are trapped within the magnetic field, while the other components of the bead-mixture slug continue to flow along the tube. The flow rate and magnetic field are controlled to ensure that sufficient residency times are allowed for the biochemical process to be undertaken. The flowing fluids continue along the conduit, binding products to the beads and removing all the unbound molecules from the paramagnetic beads. The continuous flow of slugs brings oil or air slugs, which are used as a buffer to prevent mixing of the aqueous based slugs, for example and not limited to the bead-mixture, ethanol, and dilution buffer slugs. The ethanol slug cleans any remaining contaminants from the paramagnetic beads. This cleaning step may be repeated depending on the protocol of initial slug pickup sequence. After the ethanol slug has passed an oil buffer passes prior to the slug of elution buffer to prevent any trace elements of ethanol along the tube from mixing with the elution buffer slug. The elution buffer then flows over the paramagnetic beads releasing the biomolecule targets from the paramagnetic beads in to the elution buffer slug. The slug continues to flow along the tube for further biological processing and analysis.

Slugs drawn into the system can include and are not limited to the following; bead-mix; oil; elution buffer; ethanol; water; air; sample; biochemistry mix (reagents, enzymes, etc), bead functionalisation mix; glucose; buffer; additives; optical markers; fluorescent markers; and cells.

Slug sequences used within the device include and are not limited to the following:

Bead mix and sample-oil-elution buffer.

Bead mix and sample-oil-elution buffer.

Bead mix and sample-air-oil-elution buffer.

Bead mix and sample-air-ethanol-oil-elution buffer.

Bead mix and sample-oil-ethanol-oil-elution buffer.

Bead mix and sample-air-ethanol-air-ethanol-air-oil-elution buffer.

Bead mix and sample-oil-ethanol-oil-ethanol-air-oil-elution buffer.

Bead mix and sample-oil-ethanol-oil-ethanol-air-oil-biochemical mix-oil-elution buffer.

Bead mix-oil-sample-oil-ethanol-air-oil-biochemical mix-oil-elution buffer.

Bead mix-oil-bead functionalisation mixture-oil-suspension buffer

Bead mix-oil-bead functionalisation mixture-oil-sample-oil-ethanol-air-oil-biochemical mix-oil-elution buffer.

These sequences and others may include an additional step (i.e., slug passage) for the removal of the beads from the system. This step may be performed with a controller and a perturbation in the magnetic field along the tube.

In one embodiment optical detection is used at the magnetic field source.

In one embodiment optical detection is used upstream of the magnetic field source for the analysis of slugs.

In one embodiment optical detection is used downstream of the magnetic field source for the analysis of slugs.

In one embodiment multiple parallel lines of capillary tubes are used past a single magnetic field.

In one embodiment multiple parallel lines of capillary tubes are used past a number of localised magnetic fields.

In one embodiment at least one or more lines of conduit are assembled together in a cassette for integration into a system with a pump and controller.

In one embodiment the elution buffer with the target molecules is dispensed into a composite liquid cell for further biochemistry processing and analysis.

In one embodiment, disposable capillary tubes are used. These tubes are replaced for each sample process.

In one embodiment, the conduit is reusable.

In one embodiment, where the conduit is reusable steam is used within the system to decontaminate and clean the system.

In one embodiment, where the conduit is reusable bleach is used within the system to decontaminate and clean the system.

In one embodiment, where the conduit is reusable commercial DNA digestion enzymes are used within the system to decontaminate and clean the system.

Some embodiments encompass a sample handling system having a paramagnetic bead and sample-fluid input, an immiscible fluid input, an elution buffer input, a fluid conduit, a magnetic field source, a liquid handling system, and a controller operably connected to the liquid handling system and magnetic field source. In some embodiments the controller may be programmed to: (1) draw a slug of paramagnetic beads and sample (a) past a magnetic field source, (b) where the paramagnetic beads and bound target biomolecules are captured (c) and the remaining sample contents continue to flow within the slug past the magnetic field source; (2) draw a slug of immiscible fluid; (3) draw a slug of elution buffer, (a) past a magnetic field source, (d) where the bound target biomolecules are released into the elution buffer from the paramagnetic beads in the magnetic field (e) and the slug continues to flow within the conduit for dispensing or further analysis. Exemplary flow charts are shown in FIGS. 4-6, 12-18.

In some embodiments the liquid handling system comprises a conduit and driver. In some embodiments the controller may be programmed to actuate the driver to cause the conduit to carry out steps (1) and (2), then to draw a slug for cleaning protocol, which is generally an ethanol slug, and then carry out steps (3) and (4) (FIG. 5). In some embodiments the controller may also be programmed to actuate the driver to cause the conduit to after step (5) and before step (3), to (6) draw in a slug of biochemistry reagents. (FIG. 6).

Figure 12:
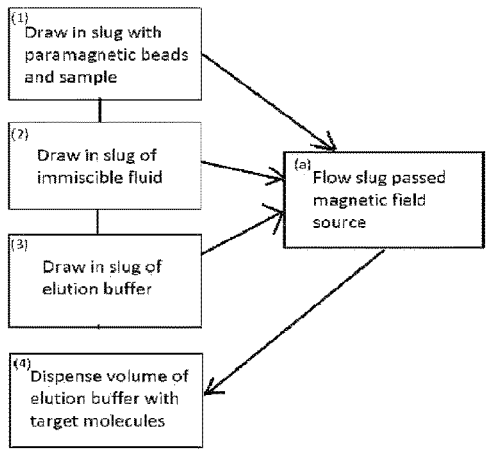
FIG. 12 illustrates a method that can be implemented as controller programming.
Figure 13:
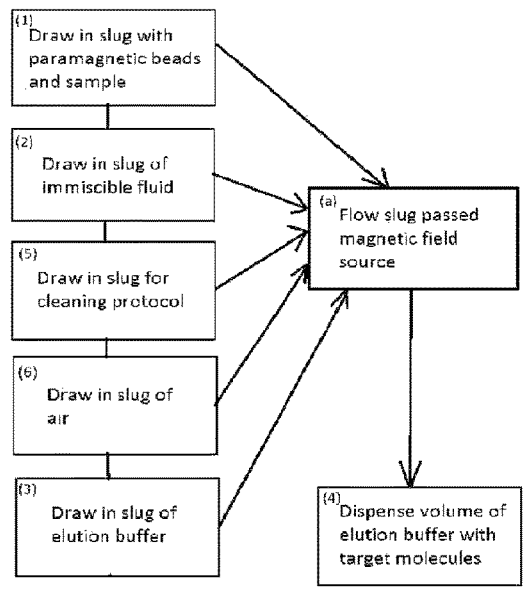
FIG. 13 illustrates a method that can be implemented as controller programming.

In some embodiments the magnetic field source comprises a fixed magnet. In some embodiments the controller may be programmed to actuate the driver to cause the conduit to carry out steps (1), (2), (3) and (4) and draw (a) the slug past the magnetic field source (FIG. 12). In some embodiments the controller may be programmed to actuate the driver to cause the conduit to carry out steps (1), (2), (5), (6), (3), and (4) while performing operation (a) (FIG. 13).

Figure 14:
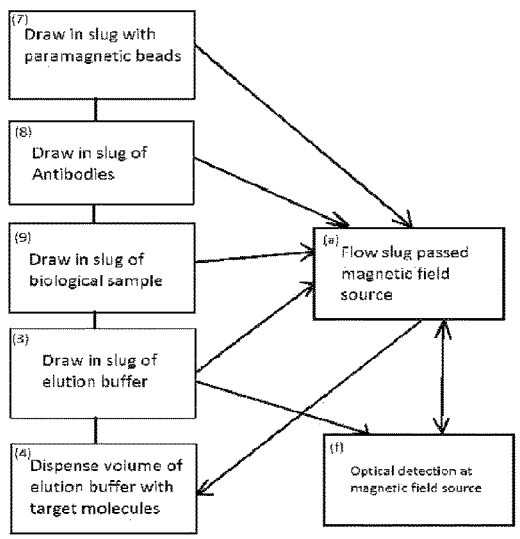
FIG. 14 illustrates a method of cell enrichment with optical analysis that can be implemented as controller programming.
Figure 15:
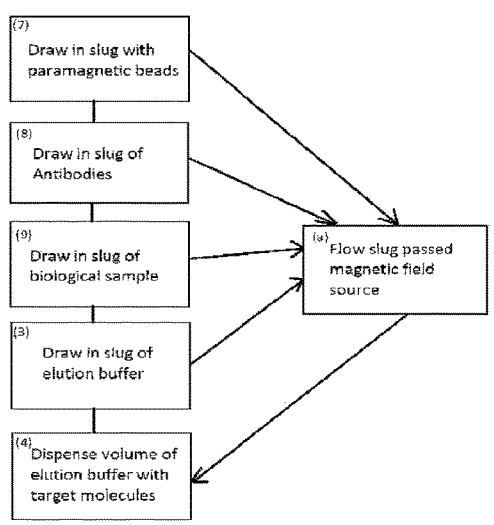
FIG. 15 illustrates a method of cell enrichment that can be implemented as controller programming.

In some embodiments the controller may be programmed to actuate the driver to cause the conduit to (7) draw in a slug of paramagnetic beads, and (8) draw in a slug of antibodies and (9) draw in a slug of biological sample and then step (3) while performing operations (a) and (0 optical detection at the magnetic field source, followed by step (4) (FIG. 14). In some embodiments the controller may not perform operation (f) (FIG. 15).

In some embodiments the magnetic field source comprises a variable state magnetic field source.

Figure 16:
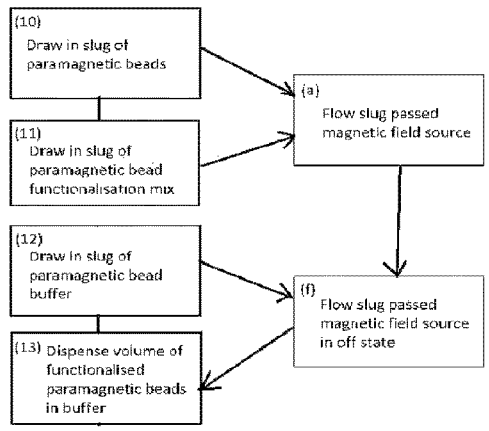
FIG. 16 illustrates a method of functionalising paramagnetic beads that can be implemented as controller programming.

In some embodiments the controller may be programmed to actuate the driver to cause the conduit to (10) draw in a slug of paramagnetic beads and then (11) draw in a slug of paramagnetic bead functionalization mix while performing operation (a), then to (12) draw in slug of paramagnetic bead buffer and for the controller to change the state of the magnetic field source to perform (f) flow the slugs past the magnetic field source in the off state before (13) dispensing a volume of functionalised paramagnetic beads in a buffer (FIG. 16).

Figure 17:
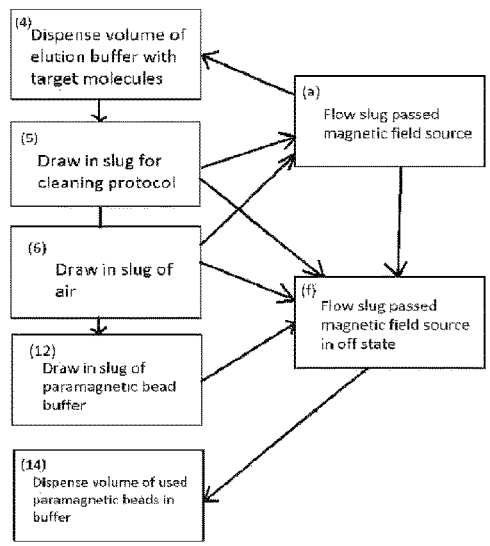
FIG. 17 illustrates a method of cleaning and removing used paramagnetic beads that can be implemented as controller programming.
Figure 18:
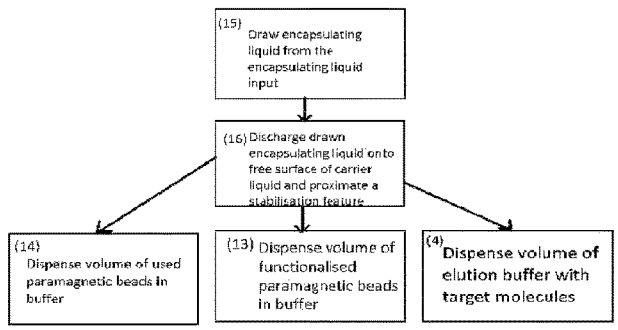
FIG. 18 illustrates a method of interaction with composite liquid cell technology that can be implemented as controller programming.

In some embodiments the controller is further programmed to following step (4), (5) and (6) while performing (a), to (12) draw a slug of paramagnetic bead buffer and change the magnetic field source to perform (f) followed by steps (5) and then (6) before (14) dispensing a volume of used paramagnetic beads in a buffer solution (FIG. 17).

In some embodiments the controller is further programmed to (15) draw encapsulating liquid from the encapsulating liquid input and (16) discharge the drawn encapsulating liquid onto a free surface of a carrier liquid and proximate to a stabilisation feature before step (4). In some embodiments the controller may be programmed to carry out step (13) or step (14) instead of step (4).

The capillary bead-based purification offers a number of advantages compared to the standard protocol. The automated fashion of the cleanup eliminates hands-on time, significantly reducing the total protocol time. It is believed that the approach can also improve the repeatability of the DNA purification steps. The microfluidic capillary approach permits cleanup of nanoliter volumes without the significant volume losses associated with pipetting small volumes. This permits processing of extremely small sample volumes and reduces reagent consumption. Another critical factor in standard purification protocols is the variability induced by the user. The present systems and methods remove this variability from the purification protocol.

Applications

Capillary Cleanup and Composite Liquid Cell Processing

In one embodiment, the elution buffer with the target biomolecules is dispensed into an immiscible fluid cell positioned on a free surface of a mutually immiscible carrier fluid. The resulting composite fluid cell can be transported, and/or merged, and/or mixed, and/or have biochemical processing performed on it.

In one embodiment, the elution buffer with the target biomolecules is dispensed into an immiscible fluid cell positioned on a free surface of a mutually immiscible carrier fluid with a mechanical stabilisation feature.

In one embodiment, the sequences of fluids drawn in to the conduit generate a composite liquid cell upon dispensing on to a free surface of a mutually immiscible carrier fluid, from the conduit.

In one embodiment, the paramagnetic beads are dispensed following a conduit cleaning protocol into a composite liquid cell for re-functionalisation of the surface.

In one embodiment, the fluid drawn into the conduit for processing is a composite liquid cell.

In one embodiment the composite liquid cell drawn into the system has paramagnetic beads and buffer.

In one embodiment, the composite liquid cell drawn into the system contains the initial sample.

In one embodiment, the composite liquid cell drawn into the system contains the elution buffer for releasing the target biomolecules.

In one embodiment, the composite liquid cell drawn into the system contains a biochemistry mix for processing on the paramagnetic beads at the magnetic field source in the conduit.

In one embodiment, the composite liquid cell technology is used to merge the paramagnetic beads and the initial sample. The composite liquid technology prevents contamination and allows for the ease processing and/or incubation; and/or storage; and/or transport; and/or mixing of the sample prior to purification.

In one embodiment, multiple composite fluid cells are generated by parallel.

Examples of composite liquid cell systems to which the present systems and methods can be adapted are disclosed, for example, in PCT/IE2011/000040, which is hereby incorporated herein by reference.

Some methods for handling a sample liquid containing magnetic particles and an immiscible encapsulating liquid include: flowing the encapsulating liquid in a conduit; flowing the sample liquid in the conduit so that the sample liquid is (a) surrounded by the encapsulating liquid and (b) located at a predetermined trapping site within the conduit; immobilizing the magnetic particles at the trapping site by applying a magnetic field at the trapping site; and flowing an elution liquid in the conduit so that (a) the elution liquid is surrounded by the encapsulating liquid, (b) the sample liquid is flowed away from the trapping site, and (c) the elution liquid is flowed to the trapping site and surrounds the immobilized magnetic particles. Target molecules can be bound to the magnetic particles. The binding may occur in the sample liquid prior to flowing the sample liquid, or at other points in the process or in another liquid medium. Target molecules, e.g., biomolecules, can also be freed (unbound) from the magnetic particles by surrounding the particles with the elution liquid. The particles may or may not be mobilized during the process. For example, the particles may be mobilized when the sample liquid is at the trapping site, when the elution liquid is at the trapping site, or when another fluid is at the trapping site. The method can also include mobilizing the magnetic particles in the elution liquid, and flowing the elution liquid away from the trapping site along with the magnetic particles and/or freed target molecules. The elution liquid can also be flowed away from the trapping site with the target molecules while the magnetic particles remain immobilized.

Methods can also include flowing one or more cleaning fluids in the conduit to the trapping site so that (a) the cleaning fluid is surrounded by the encapsulating liquid, and (b) the cleaning fluid surrounds the immobilized magnetic particles. The magnetic particles may be mobilized in the cleaning fluid while the cleaning fluid is at the trapping site. The cleaning fluid can also be flowed in the conduit away from the trapping site. If mobilized, the magnetic particles can be carried along with the cleaning fluid. Alternatively the magnetic particles can be mobilized in the cleaning fluid at the trapping site, then immobilized again. Then the cleaning fluid can be flowed in the conduit away from the trapping site while the magnetic particles remain at the trapping site. A second cleaning fluid can also be flowed in the conduit.

Some methods for handling a first sample liquid containing magnetic particles, a second sample liquid, and an encapsulating liquid, both sample liquids being immiscible with the encapsulating liquid, include: flowing the encapsulating liquid in a conduit; flowing the first sample liquid in the conduit so that the first sample liquid is (a) surrounded by the encapsulating liquid and (b) located at a predetermined trapping site within the conduit; immobilizing the magnetic particles at the trapping site by applying a magnetic field at the trapping site; flowing the first sample liquid in the conduit so that the first sample liquid is flowed away from the trapping site while the magnetic particles remain immobilized at the trapping site; and flowing the second sample liquid in the conduit so that the second sample liquid is (a) surrounded by the encapsulating liquid and (b) surrounds the immobilized magnetic particles.

The second sample liquid can contain target molecules, e.g., biomolecules, that bind to the magnetic particles when the second sample liquid surrounds the magnetic particles. The magnetic particles can either remain immobilized in the second sample liquid, or can be mobilized in the second sample liquid. Methods can also include, after flowing the second sample liquid, flowing an elution liquid in the conduit so that (a) the elution liquid is surrounded by the encapsulating liquid, (b) the second sample liquid is flowed away from the trapping site, and (c) the elution liquid is flowed to the trapping site and surrounds the immobilized magnetic particles. Flowing the elution liquid can include freeing the target biomolecules from the magnetic particles by surrounding the magnetic particles with the elution liquid. The magnetic particles can either be mobilized in the elution liquid or remain immobilized in the elution liquid.

Methods can also include using a cleaning fluid, for example: after flowing the second sample liquid, flowing a first cleaning liquid in the conduit so that (a) the first cleaning liquid is surrounded by the encapsulating liquid, (b) the second sample liquid is flowed away from the trapping site, and (c) the first cleaning liquid is flowed to the trapping site and surrounds the immobilized magnetic particles; and after flowing the first cleaning liquid, flowing an elution liquid in the conduit so that (a) the elution liquid is surrounded by the encapsulating liquid, (b) the first cleaning liquid is flowed away from the trapping site, and (c) the elution liquid is flowed to the trapping site and surrounds the immobilized magnetic particles.

In any of the methods disclosed herein, the sample liquid and encapsulating liquid may constitute a composite liquid cell at some point during, or throughout, the disclosed method. Similarly, in any of the disclosed methods, markers may be used in conjunction with the target molecules. Such markers can be detected by optical or fluorescent interrogation of the trapping site. In any of these methods, the conduit could, for example, be a capillary tube.

A liquid handling system can include a conduit having a predetermined trapping site, a pump configured to apply positive pressure, negative pressure, or no external pressure to a location in the conduit, a magnetic field source configured to apply a magnetic field at the trapping site when activated and substantially no magnetic field when not activated, and a controller operably attached to the pump and the magnetic field source so that the controller can activate the pump and/or the magnetic field source. The controller can be programmed to: activate the pump so that an encapsulating liquid is flowed in the conduit; activate the pump so that a sample liquid is flowed in the conduit in such a way that the sample liquid is (a) surrounded by the encapsulating liquid and (b) located at the trapping site within the conduit, the sample liquid containing magnetic particles; activate the magnetic field source so that the magnetic particles are immobilized at the trapping site; and activate the pump so that an elution liquid is flowed in the conduit in such a way that (a) the elution liquid is surrounded by the encapsulating liquid, (b) the sample liquid is flowed away from the trapping site, and (c) the elution liquid is flowed to the trapping site and surrounds the magnetic particles. More generally, the controller may be programmed to activate the pump and activate and/or deactivate the magnetic field source, so as to carry out any of the disclosed methods. The conduit can be, for example, a capillary tube. The pump can be configured to apply positive pressure and/or negative pressure to the conduit. For example, the pump may be configured to flow a fluid in the conduit in one direction under positive pressure and flow a fluid in the conduit in another direction under negative pressure.

Sequencing

Many next generation sequencing (NGS) platforms require DNA libraries made up of DNA fragments within a specific range of base pair lengths. In addition, these DNA fragments need to be tagged with specific nucleotide sequences (adapters) to allow the sequences to be amplified using PCR and to allow the library fragments to anneal to the sequencer flow cell. Sequence specific indices can also be added to the DNA fragments to identify individual samples when multiplexing sample within a single flow cell. The tagmentation of DNA (DNA is fragmented and tagged with adapters) and the addition of common adapters and indices is achieved in two separate biological reactions. Following these reactions, the DNA library is cleaned to remove excess nucleotides, enzymes, primers, salts and other contaminants. Consequently, the workflow required to tagment DNA, purify tagmented DNA, add common adapters and indices and purify the final library product is complex and labour intensive. In one embodiment the capillary-based cleanup system can be used to automate the sample purification and DNA isolation steps required within genetic sequencing. A complete example of this process is disclosed below.

Genetic Sequencing Bead Coating

Genetic sequencing bead preparation is a process by which small beads are coated in an application-specific chemistry. In one embodiment the coating of beads in advance of genetic screening is achieved by flowing a bead mix slug followed by the specific primer chemistry used to coat the beads within the conduit past the stationary magnet field. An elution buffer slug is then passed in which the bead concentration can be controlled by the volume of elution buffer used within the slug. The magnetic field is removed and the functionalised bead mix flows along the conduit for further processing.

In one embodiment the flow within the conduit can be reversed and the functionalised bead mix is dispensed for storage or further biochemical processing.

These methods provide for a convenient way of manipulating and combining sub-microliter volumes of fluid that is currently not possible to achieve using conventional techniques, thereby reducing the initial sample volumes and improving the bead coating efficiency by reducing the reaction volume. Further processing using PCR and thermal cycling and genetic sequencing is application-specific.

The use of this technology greatly simplifies the collection procedure for these relatively small target volumes. The system facilitates 100% volume retrieval as the biological sample in processing does not incur any pipetting loses. These features make automation of the biochemistry process easier to facilitate.

Size Selection of Small RNAs

Sequencing of small RNA molecules is complicated by the overwhelming amount of background non-specific product after reverse transcription, the length of which is marginally smaller than that of the small target molecules. Currently, the small target cDNA molecules (reverse transcribed from RNA) are size selected by excising the desired gel electrophoresis band. Typically, the DNA from the gel slice is extracted, added to a PCR reaction and then cleaned using a spin column based approach. The workflow is labour intensive and the DNA yield/recovery rate is poor.

In one embodiment the purification and size selection is achieved by pumping the necessary reagents in a capillary. Specific volumes of DNA bead solution, ethanol, air and elution buffer are drawn and flow within a conduit. As the DNA-bead solution flows through a magnet field, the beads and bound DNA are removed from solution to form a pellet at the conduit wall. The bead-DNA pellet is washed as the subsequent ethanol slugs flow past the immobilised pellet. DNA is then eluted off the beads and into solution as the elution buffer flows past the bead pellet. The pumps are reversed and the elutant containing purified DNA is recovered for the subsequent steps of the NGS library preparation workflow.

In one embodiment, paramagnetic beads are mixed with cDNA product. Using the size selection properties of the magnetic beads by selecting specific buffer conditions (different sizes of DNA can be bound by using different buffer conditions), the small cDNA molecules can be exclusively bound to the beads while the remaining molecules remain in solution and delivered to waste. The small target molecules are then eluted as the elution buffer passes the fixed bead pellet.

In one embodiment the size selection process is preformed with out ethanol slugs.

Size Selection of DNA Libraries for NGS Sequencing

Each of the next generation sequencers have an optimal read length (base pairs). During library construction, DNA is fragmented into DNA molecules with a wide base pair length range. Size selection is currently performed using paramagnetic beads on a microtitre plate and is labour intensive and suffers from inefficiencies from pipetting errors and user protocol variations. The capillary-based conduit system can be used for size selection of DNA libraries.

Nucleic Acid Purification

The capillary-based conduit system can be used for purification and/or isolation of samples before and/or after PCR. The paramagnetic beads are used as sites for the purification and/or isolation of the nucleic acid.

Paramagnetic beads can be used to remove excess unincorporated deoxynucleotide triphosphates, salts and enzymes after PCR. Efficient removal of these contaminants is required to ensure success in downstream applications such as genotyping, Sanger and next generation sequencing. Bead-based purification offers high recovery rate of amplicons, efficient removal of contaminants and flexibility in the cleanup. Examples of some of the possible embodiment methods are given below.

Protein Enrichment

Protein enrichment can also be performed using the capillary-based conduit system. The paramagnetic beads are used as sites to enrich target proteins.

The beads are coated with a media with a high affinity to antibodies. Antibodies specific to a target protein are added to the beads, coupling to the binding sites located on the bead surface. Biological samples containing target proteins are then added, attaching to the antibodies. Applying a magnetic field permits separation and isolation from the biological sample containing background molecules. Discarding the supernatant and adding an elution buffer yields purified target protein. The bead-based protein enrichment approach can be achieved using the capillary-based system, permitting protein enrichment in an automated, high-throughput fashion.

Build Synthetic Nucleic Acid Structures:

Paramagnetic beads may be used in systems similar to that outlined here to assist in assembling nucleic acid structures (oligonucleotides).

Magnetic beads provide large surface to volume ratios important in exposing relevant bound chemistry. Oligonucleotide synthesis is carried out by a stepwise addition of nucleotide residues to the 5'-terminus of the growing chain until the desired sequence is assembled. Steps include, de-blocking (detritylation) where functional groups are removed by an acid solution prior to coupling. Coupling introduces and binds nucleoside phosphoramidite to build the next base. Capping then ensues to prevent further chain elongation. This is usually performed by treating the solid supports with acetic anhydride and 1-methylimidazole. Oxidation is then performed to increase stability.

Cell Enrichment/Isolation

Paramagnetic beads can be used to isolate and enrich target cells from a biological sample. This approach enriches cells directly from the biological sample without using columns, ensuring high cell viability and yield. This is particularly important in applications such as tumour cells analysis in minimal residual disease where target cells are extremely rare.

Enrichment is achieved by adding paramagnetic beads coated with antibodies against specific cell markers to a biological sample. The target cells are bound to the beads and separated using a magnet. The supernatant containing background cells is then discarded. The target cells can then be recovered for analysis. This paramagnetic bead based cell isolation and enrichment approach can be implemented in a capillary-based system, permitting automated cell enrichment and integration with other microfluidic technologies for downstream analysis.

EXAMPLES

The following examples illustrate particular embodiments, but should not be viewed as limiting the scope of the disclosed subject matter.

Purification and Recovery of a 285 bp Amplicon

This example presents data from GenCell Biosystems' capillary-based nucleic acid purification system. This experiment was conducted to demonstrate that the capillary purification system was capable of purifying and recovering PCR product.

Forward and reverse primers targeting a 285 bp fragment on the actin-beta gene were used to amplify the intended product using PCR. This product was then used to evaluate the performance of the capillary-based paramagnetic bead purification instrument. 18 µL of bead-buffer mix (AMPure Xp, Agencourt) was pipetted to 10 µL of PCR product in a PCR tube. The 1.8× bead-mix concentration ensures that fragments greater than 100 bp are recovered. The bead-DNA mix was pipette mixed and incubated at room temperature for 5 minutes to allow DNA to bind to the beads, as recommended by the AMPure Xp protocol. The 28 µL bead-DNA solution was aspirated into a PTFE capillary tube (400 micron internal diameter), followed by two 5 µL slugs of 70% ethanol, a 10 µL slug of air, 2.5 µL of polydimethylsiloxane oil and 10 µL of elution buffer (nuclease free water). The sequence of DNA-bead mix, ethanol, air, oil and elution buffer slugs were pumped at a constant flow rate of 10 µL/min using a syringe pump (PHD 2000, Harvard Apparatus). The described sequence of reagents mimicked the purification steps specified by the AMPure Xp protocol. The beads and bound target DNA were removed from the bead-DNA solution to the wall of the capillary as the solution passed a magnet. The ethanol slugs passed over the now fixed DNA-bead pellet, washing the pellet and removing residual contaminants. The air and oil slugs were then delivered past the pellet, removing residual ethanol. In the final step of the purification process, the elution buffer slug eluted the target DNA from the beads and into solution as it passed the bead pellet. The pump was reversed and the elutant was recovered in a sterile PCR tube for analysis. This experiment was performed in duplicate. The elutants were then analysed using gel electrophoresis.

Figure 10:
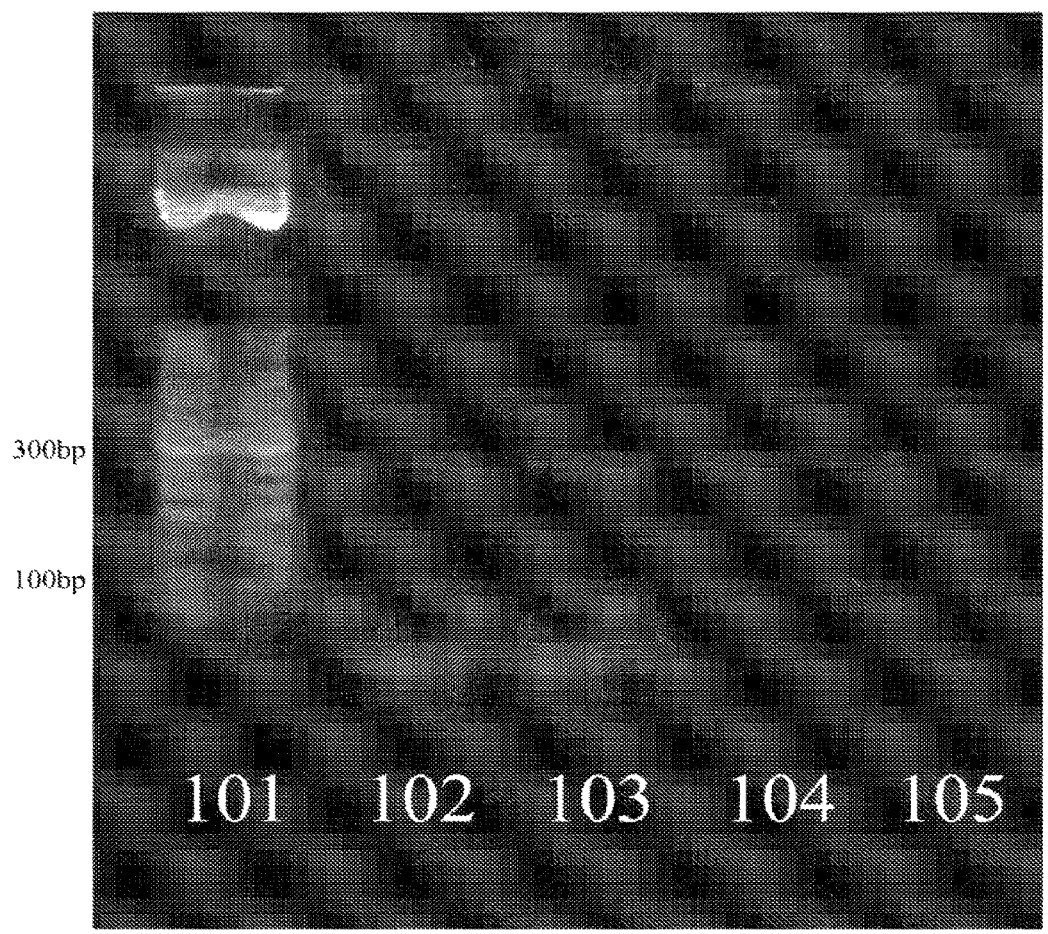
FIG. 10 shows a gel result confirming recovery of 285 bp amplicon using bead-based purification in a capillary. Comparing unpurified products (lanes 102, 103) to purified products (lanes 104, 105), it is clear that non-specific products such as primer dimer were successfully removed (lane 101 is a ladder).

A gel electrophoresis result comparing the two elutant samples to un-purified 285-bp actin-beta product can be seen in FIG. 10. Observing FIG. 10, it is clear that the described capillary purification technique successfully recovered the 385 bp. Comparing the elutant bands to the uncleaned PCR product bands, it is evident the purification procedure removed non-specific products such as primer-dimer.

DNA Recovery Rates: Comparison with Conventional DNA Isolation Protocols

This example presents data from the GenCell Biosystems capillary nucleic acid purification system, comparing the recovery rates between the conventional bead-based purification protocol and the capillary bead-based purification protocol. These experiments were used to evaluate the performance of the capillary bead-based purification approach.

The 285 bp actin-beta amplicon was used as the DNA template for purification. The amplicon was purified and recovered following the capillary bead-based purification protocol outlined above in the example Purification and Recovery of a 285 bp Amplicon. This experiment was performed in quadruplicate and the elutant samples were stored for analysis.

In a separate experiment, 10 µL of the template solution containing the 285 bp amplicon was cleaned following the AMPure Xp protocol. 18 µL of AMPure Xp bead mix was pipetted to a well of a 96-well microtitre plate containing 10 µL of the template solution. The DNA-bead mixture was pipette mixed and incubated at room temperature for 5 minutes. The microtitre plate was placed on a magnetic plate to separate beads containing bound DNA from the solution. The supernatant was aspirated using a pipette and discarded. 200 µL of 70% ethanol was added to the bead pellet and incubated for 30 seconds at room temperature. The ethanol was then aspirated out using a pipette and discarded. This was repeated for a total of two washes. Following the final wash step, the pellet was allowed to dry to ensure all traces of ethanol are removed. 10 µL of elution buffer (nuclease free water) was added to the well and pipetted to the bead pellet off the magnetic plate, eluting DNA off the beads and into solution. The microtitre plate was placed on the magnetic plate and the elutant was transferred to a new plate. This experiment was performed in triplicate and the samples were stored for analysis.

Figure 7:
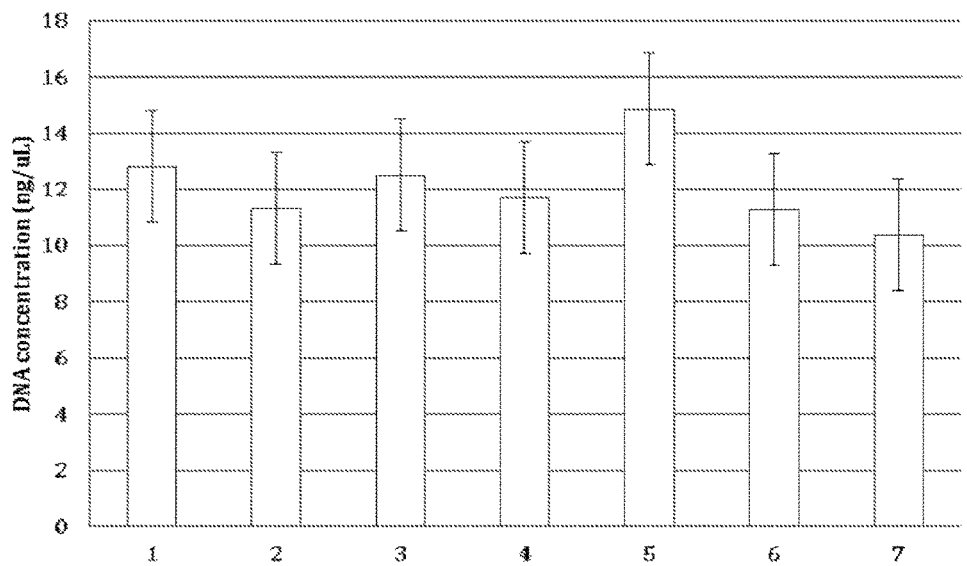
FIG. 7 shows spectrophotometry results demonstrating comparable recovery rates between the control protocol and the capillary cleanup protocol. The concentration of recovered/eluted DNA (actin-beta amplicon) is plotted for both the control bead-based purification and the capillary bead-based purification.

The elutants recovered from the conventional cleanup protocol and the capillary cleanup approaches were quantified using UV-vis spectrophotometry measurements (NanoDrop 2000, Thermo Scientific). The UV-vis spectrophotometry quantification results can be seen in FIG. 7. The quantification results shown in FIG. 7 demonstrate that the capillary cleanup recovery rates are identical to those achieved using the conventional protocol. This result confirms that the DNA recovery rate is equal to that achieved using the conventional AMPure Xp protocol. The capillary DNA purification approach outlined here offers highly automated purification without a trade-off in performance.

DNA Library Preparation

This example illustrates how capillary bead-based purification can be incorporated into a DNA library preparation protocol for next generation sequencing. The data presented here demonstrates that the purification steps currently performed after various biological processes within a DNA library preparation protocol can be replaced using the capillary cleanup approach, offering a fully automated, high-throughput approach to DNA library preparation for next generation sequencers.

In this example, the capillary cleanup was implemented in lieu of the clean-up steps currently used in Nextera Sample Prep Kit (Illumina). A 9 µL tagmentation reaction was prepared. This reaction contained control genomic DNA, high molecular weight buffer, Nextera enzyme mix and nuclease free water. In this reaction, DNA is fragmented and tagged with adapters. The tagmentation reaction was prepared and incubated at 55° C. for 5 minutes. Following tagmentation, the sample was purified using the capillary bead-based purification system in place of the recommended Zymo DNA clean and Concentrator Kit (Zymo Research). 9 µL of tagmented product was added to 16.2 µL of AMPure Xp bead solution, pipette mixed and incubated at room temperature for 5 minutes. The DNA-bead solution was then aspirated into a PTFE capillary (400 micron internal diameter). The capillary was then loaded with 2.5 µL of air, a 10 µL slug of DNA binding buffer, a 2.5 µL slug of air, two 5

μL slugs of ethanol, separated by a 2.5 μL slug of air, a 10 μL slug of air, a 2.5 μL slug of oil and a 15 μL slug of elutant buffer (nuclease free water). The train of reagent slugs was pumped at 10 μL/min using a syringe pump (PHD2000, Harvard). The beads and bound target DNA were removed from the bead-DNA solution to the wall of the capillary as the solution passed a magnet. The DNA-binding buffer (Zymo Clean and Concentrator Kit, Zymo Research) then passed the immobilised bead pellet, dissociating the transposase enzyme from the fragmented target DNA—a known PCR inhibitor. Following this, the ethanol wash steps passed the bead-DNA pellet, removing residual contaminants. The air and oil slugs then passed the pellet, removing residual ethanol. Finally, the tagmented DNA was eluted off the beads as the elution buffer passed the pellet. The pump was reversed and the elution buffer recovered for subsequent steps of the Nextera library preparation protocol.

11 μL of the elution was added to a PCR reaction (25 μL final volume). Limited cycle PCR was then performed using a GeneAmp PCR System 9700 (Applied Biosystems), according to the thermal cycling conditions specified by the Nextera protocol. The PCR reaction was heated to 72° C. for 3 minutes, 95° C. for 30 seconds, followed by 9 cycles of 95° C. for 10 seconds, 62° C. for 30 seconds, 72° C. for 3 minutes. During the PCR step, bridge PCR compatible sites and specific indexes are added to the ends of the tagmented DNA. Following the limited cycle PCR step, the DNA library product was purified using the capillary bead-based cleanup in place of the recommended Zymo DNA Clean and Concentrator Kit (Zymo Research) or AMPure Xp purification kit. 15 μL of the 25 μL PCR reaction was added to 25 μL of AMPure Xp bead solution, pipette mixed and incubated at room temperature for 5 minutes. The bead-DNA solution was aspirated into a PTFE capillary (400 micron internal diameter). The capillary was then loaded with 2.5 μL of air, two 5 μL slugs of ethanol, separated a slug of air, and followed by a 10 μL slug of air, a 2.5 μL slug of oil and a 15 μL slug of elutant buffer (nuclease free water). The beads and bound target DNA were removed from the bead-DNA solution to the wall of the capillary as the solution passed a magnet. Following this, the ethanol wash steps passed the bead-DNA pellet, removing residual contaminants. The air and oil slugs then passed the pellet, removing residual ethanol. Finally, the DNA library sequences were eluted off the beads as the elution buffer passed the pellet. The pump was reversed and the elution buffer recovered for analysis. This experiment was performed in duplicate.

Figure 8:
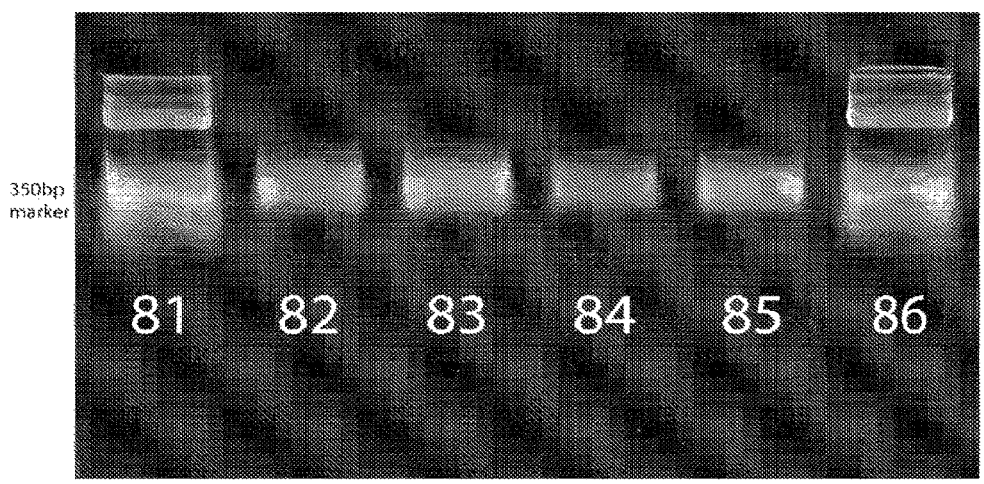
FIG. 8 shows a gel image showing Nextera product smears for control cleanup and capillary cleanup.

The recovered DNA libraries were analysed using gel electrophoresis. The gel electrophoresis result can be seen in FIG. 8. Examining the gel result, it is clear that the two capillary cleanup steps implemented into the Nextera protocol successfully cleaned and purified the library sequences. Smeared bands corresponding to DNA library fragments greater than 200 bp can be seen in FIG. 8, demonstrating that the capillary bead-based clean is effective at removing the transposase enzyme after tagmentation and purifying products after tagmentation and limited cycle PCR. This that verifies that capillary bead-based cleanup system is a feasible alternative to the conventional purification steps within a DNA library preparation protocol.

DNA Library Preparation: Comparison with Conventional DNA Purification Protocols This example validates the capillary bead-based purification system for use in a DNA library preparation protocol. The DNA library preparation protocol was carried as per protocol and with the capillary cleanup steps. The final library product from both experiments was then compared, confirming the efficacy of the capillary clean-up steps in place of the conventional cleanup steps.

The Nextera library preparation protocol was carried out using the capillary cleanup steps after tagmentation and after limited cycle PCR, as described in the previous example DNA Library Preparation. This was performed in duplicate and the final library product was recovered and stored for analysis.

The Nextera library preparation protocol was carried out as per the recommended protocol with one alteration—the post-tagmentation cleanup was performed using the AMPure Xp purification kit. The tagmentation reaction was prepared as described in the previous example DNA Library Preparation. The 9 μL tagmentation reaction was then purified using the AMPure Xp purification kit. 9 μL of tagmented product was added to 16.2 μL of AMPure Xp bead solution in a well of a microtitre plate, pipette mixed and incubated at room temperature for 5 minutes. The microtitre plate was placed on a magnetic plate to separate beads containing bound DNA from the solution. The supernatant was aspirated using a pipette and discarded. 200 μL of DNA binding buffer was added to the bead pellet and incubated for 60 seconds at room temperature to dissociate the transpose enzyme from the tagmented DNA. 200 μL of 70% ethanol was added to the bead pellet and incubated for 30 seconds at room temperature. The ethanol was then aspirated out using a pipette and discarded. This was repeated for a total of two washes. Following the final wash step, the pellet was allowed to dry to ensure all traces of ethanol are removed. 15 μL of elution buffer (nuclease free water) was added to the well and pipetted to the bead pellet, which was removed from the magnetic plate to allow for the re-suspension of the beads in the elution buffer, eluting DNA off the beads and into solution. The microtitre plate was replaced on the magnetic plate and the beads and elutant were separated and the elutant was transferred to a PCR reaction (25 μL final volume).

Limited cycle PCR was performed, as described in the example DNA Library Preparation. Following PCR, 15 μL of the 25 μL PCR reaction was added to 25 μL AMPure Xp bead solution in a well of a microtitre plate. The DNA-bead mixture was pipette mixed and incubated at room temperature for 5 minutes. The microtitre plate was placed on a magnetic plate to separate beads containing bound DNA from the solution. The supernatant was aspirated using a pipette and discarded. 200 μL of 70% ethanol was added to the bead pellet and incubated for 30 seconds at room temperature. The ethanol was then aspirated out using a pipette and discarded. This was repeated for a total of two washes. Following the final wash step, the pellet was allowed to dry to ensure all traces of ethanol are removed. 15 μL of elution buffer (nuclease free water) was added to the well and pipetted to the bead pellet, which was removed from the magnetic plate to allow for the re-suspension of the beads in the elution buffer and the releasing the DNA off the beads and into solution. The microtitre plate was replaced on the magnetic plate to separate beads from the solution and the elutant containing the final library product was transferred to a new plate for analysis. This experiment was performed in duplicate.

The final library products recovered using the conventional protocol and the protocol with incorporated capillary cleanup steps were analysed using gel electrophoresis. The gel result can be seen in FIG. 8. Examining this gel result, it is clear that the intensity of the smear and size of the products recovered from the capillary cleanup protocol is approximately equal to that of the libraries prepared using the conventional protocol. This demonstrates that implementing the capillary bead-based purification steps into the protocol yields similar recovery rates and library quality to that obtained using the conventional protocol. The capillary-based approach offers a labour free, high-throughput approach that can be integrated with other open architecture technologies to offer a fully automated DNA library preparation system.

Low Volume DNA Library Preparation: Comparison with Conventional DNA Purification Protocols This example highlights the efficiency of the capillary bead-based purification system in preparing low volume DNA libraries. The DNA library preparation protocol was carried as per protocol and with the capillary cleanup steps for reduced reaction volumes. The final library product from both experiments was then compared, confirming the advantages of employing the capillary clean-up steps in place of the conventional cleanup steps when preparing small volume DNA libraries.

In the first part of this experiment, a 2.5 µL tagmentation reaction was prepared and incubated at 55° C. for 5 minutes. Following tagmentation, the 2.5 µL tagmentation reaction was added to 4.5 µL AMPure Xp bead solution, pipette mixed and incubated at room temperature for 5 minutes. The solution was purified using the AMPure Xp protocol with the addition of the DNA binding buffer step, as described in the previous example. The tagmented product was eluted in 1.1 µL of nuclease free water and added to the PCR reaction. The 2.5 µL PCR reaction was then purified according to the AMPure Xp protocol and the final library product was eluted in 4 µL of nuclease free water and stored for analysis. In the second part of this experiment, identical volumes were purified using capillary cleanup steps, as described in the previous example. Both approaches were performed in duplicate.

The final DNA library products were added to a 20 µL PCR reaction and analysed using quantitative PCR (qPCR). The forward and reverse primers were specific to the adapters added to the end of the DNA library fragments, ensuring that only sequencer ready fragments would be quantified. SYBR green detection chemistry was used. Standards supplied by KAPA Biosystems were also run on the same qPCR plate, permitting absolute quantification of recovered library product. The qPCR plate was subjected to 40 cycles (ABi StepOne, LifeTechnologies) according to the KAPA Biosystems Library Quant Kit.

Figure 9:
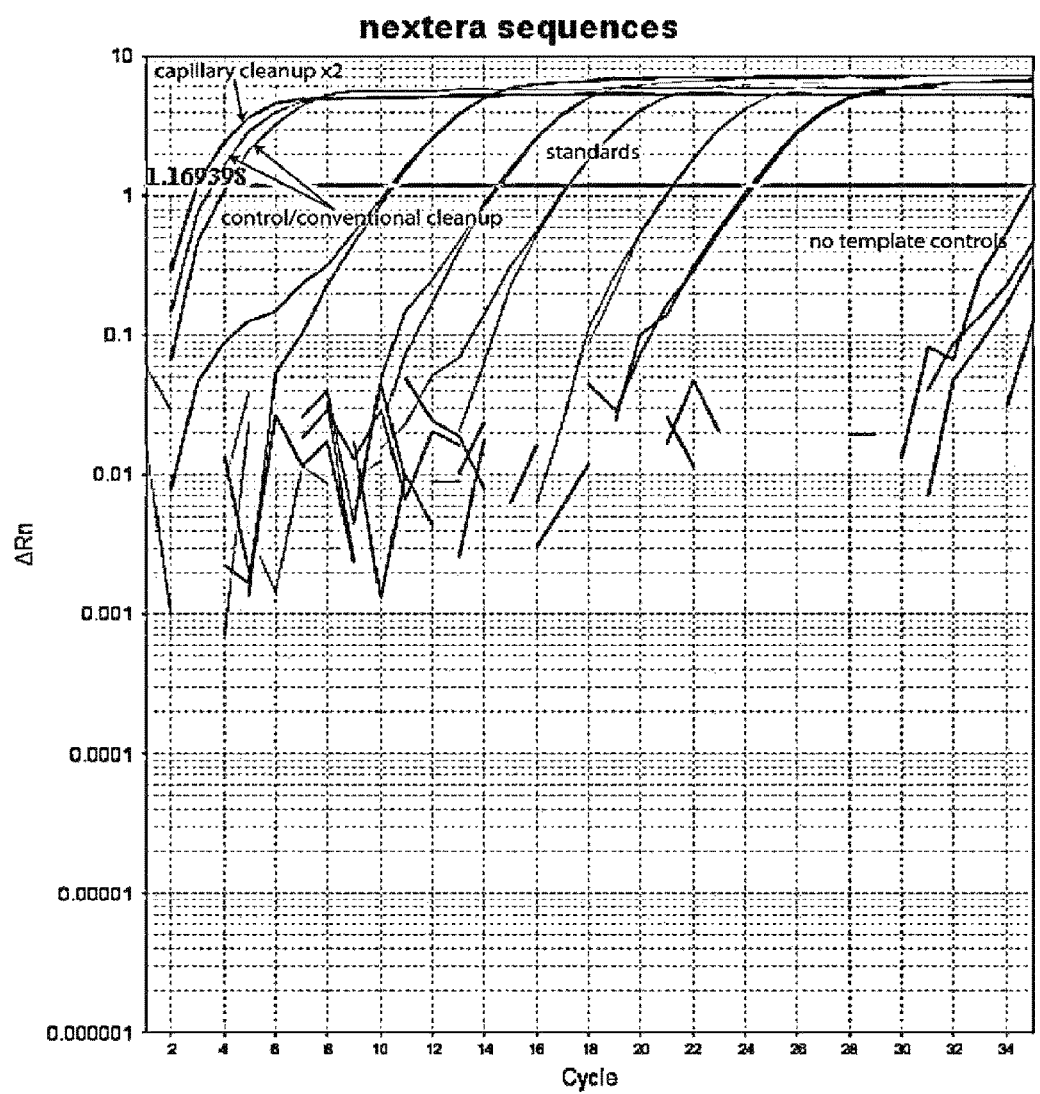
FIG. 9 shows qPCR results showing Nextera product recovered from control protocol and capillary cleanup protocol.

The qPCR result can be seen in FIG. 9. The two libraries recovered using the capillary cleanup have quantification cycle (Cq) values earlier than the libraries recovered using the conventional protocol. The Cq is defined as the cycle number at which the fluorescence signal exceeds the background fluorescence level and is related to the amount of starting product. The Cq values for the capillary cleaned product were 2.8 and 2.9. The Cq values for product cleaned using conventional methods were 3.6 and 4.0, significantly later than the capillary cleaned product. This demonstrates that capillary cleanup offers superior recovery rates when preparing DNA libraries from small volumes. This may be attributed to the reduced sample losses associated with the capillary approach in comparison to the conventional protocol where pipetting errors are significant.

The superior DNA library recovery rates associated with the capillary cleanup is supported further in the next example.

DNA Recovery from Low Sample Volumes Using Capillary Bead-Based Isolation

This example verifies that the capillary clean-up approach has excellent recovery rates when manipulating small DNA library volumes. In this example, a number of experiments were conducted to investigate the recovery of DNA library using the capillary cleanup.

The full Nextera protocol was performed, following the conventional protocol. The final DNA library product was stored and used as template. 2.5 µL of DNA library was added to 4.5 µL of AMPure Xp bead solution, pipette mixed and subjected to capillary cleanup procedure outlined in previous examples. The recovered product was added then to a PCR reaction. Positive controls containing 2.5 µL of template were run in triplicate and analysed. The recovered library product and positive controls were analysed using qPCR. The positive control and elutant Cq values are presented in table 1. The positive control Cq values represent the starting quantity of DNA library product before any purification process. Since 2.5 µL of DNA library product was used in the positive controls and inputted into the small volume capillary clean process, the Cq values for both should be equal, assuming a recovery efficiency of 100%. Examining the Cq values for the positive controls and the elutant, it is clear that most, if not all of the library product is recovered after subjecting the sample to the capillary bead-based cleanup. The elutant Cq values are approximately equal to the positive controls, demonstrating efficient recovery of DNA library product.

This example confirms that the capillary cleanup approach is capable of efficiently recovering DNA library from small volumes.

TABLE 1

|  | Test 1 | Test 2 | Test 3 | Test 4 |
| --- | --- | --- | --- | --- |
| Description | Cq | Cq | Cq | Cq |
| Positive Control 1 | 4.8 | 5.0 | 4.5 | 5.4 |
| Positive Control 2 | 5.1 | 4.9 | 4.4 | 5.3 |
| Positive Control 3 | 5.0 | 5.1 | 4.4 | 5.2 |
| Average Positive Control | 4.96 | 5.0 | 4.43 | 5.3 |
| Elutant | 4.7 | 4.7 | 6.0 | 5.3 |

Decontamination of Capillary—Reusability

The capillary cleanup procedure outlined in the previous examples typically purifies high concentration samples such as PCR product or DNA library. Inevitability, the capillary is contaminated with small quantities of target DNA as the beads are separated out of solution and held at the capillary wall. Without disposing the line, this would lead to carry-over contamination between samples. Clearly, this is highly undesirable. This example demonstrates that a series of wash steps sufficiently removes or destroys any nucleic acids that remain in the capillary after performing capillary bead-based purification—permitting reusability of the capillary.

Figure 11:
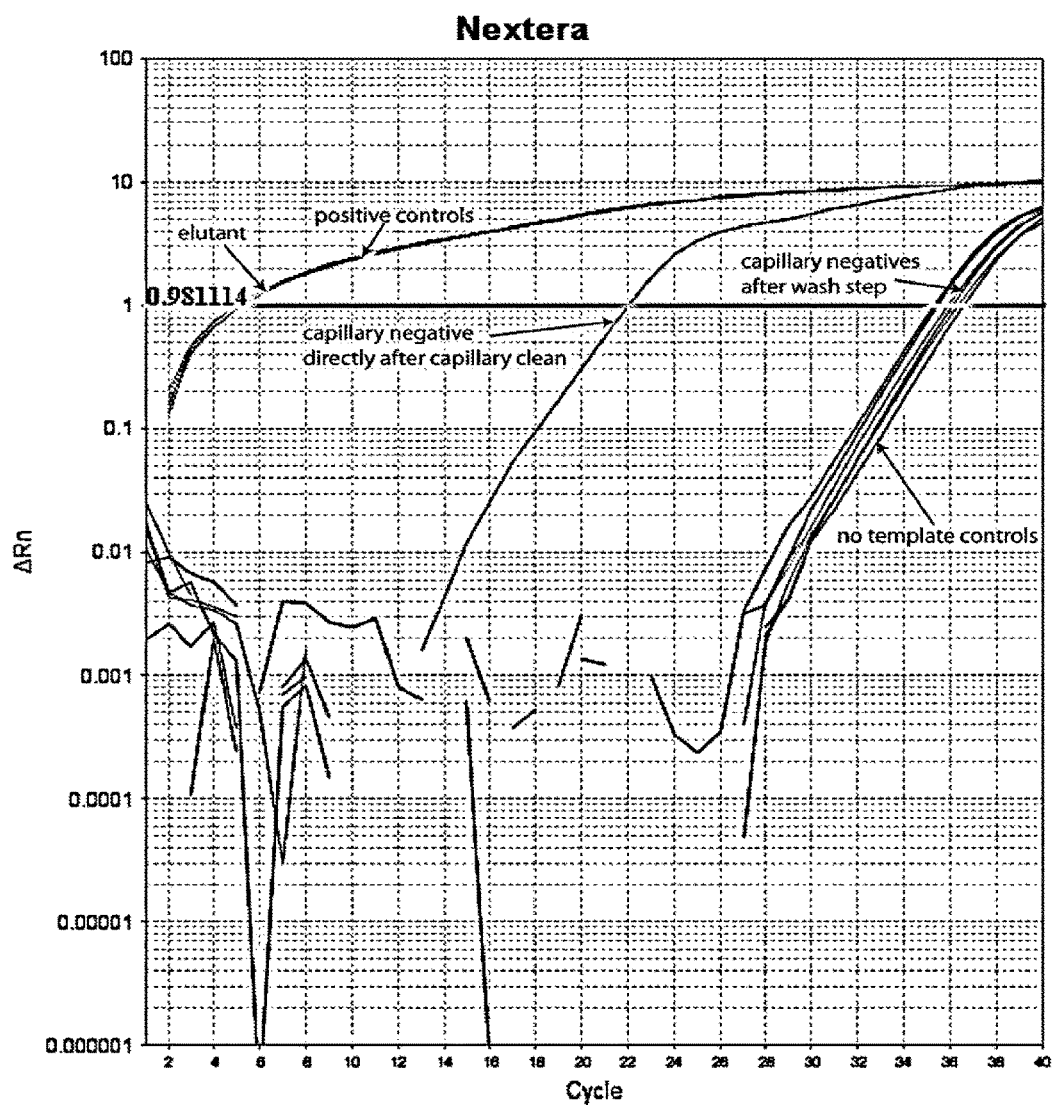
FIG. 11 shows a qPCR result of Decontamination of Capillary—Reusability Example

PCR product was purified using the capillary clean-up approach, following the exact protocol outlined in the DNA Recovery from Low Sample Volumes using Capillary bead-based Isolation example. A 9 µL capillary negative slug (nuclease free water) was then passed along the capillary and recovered to investigate whether the line was contaminated. Following this, the capillary was filled with a cleaning reagent (LookOut DNA Erase, SigmaAldrich) for 3 minutes. The cleaning reagent was pumped to waste and the line was flushed with sterile water. Following decontamination, two sterile 9 µL capillary negative slugs were passed along the capillary to investigate levels of contamination after the wash steps. The recovered elutant and capillary negatives were added to PCR reactions. Positive and no template controls were also prepared and analysed using qPCR (ABi StepOne, LifeTechnologies). The qPCR result can be seen in FIG. 11. Examining FIG. 11, it is clear that the capillary is significantly contaminated directly after performing the capillary cleanup. Following the decontamination step, the capillary negative Cq values fall within the no template control Cq values. The Cq values exhibited by the no template controls and the capillary negatives correspond to primer dimer product. The capillary negatives remain negative for target product, indicating effective decontamination after washing the capillary.

Implementing the described wash steps permits reusability of the line after each purification/size selection experiment.

Definition

In this disclosure the use of the term "slug" is interchangeable with the term plug, and indicates a discreet volume of fluid flowing within the conduit.

We claim:
1. A liquid handling system comprising:
a conduit having a predetermined trapping site,
a pump configured to apply positive pressure, negative pressure, or no external pressure to a location in the conduit,
a magnetic field source configured to apply a magnetic field at the trapping site when activated and substantially no magnetic field when not activated, and
a controller operably attached to the pump and the magnetic field source so that the controller can activate the pump and/or the magnetic field source, the controller being programmed to:
activate the pump so that an encapsulating liquid is flowed in the conduit;
activate the pump so that a sample liquid is flowed in the conduit in such a way that the sample liquid is (a) surrounded by the encapsulating liquid and (b) located at the trapping site within the conduit, the sample liquid containing magnetic particles;
activate the magnetic field source so that the magnetic particles are immobilized at the trapping site; and
activate the pump so that an elution liquid is flowed in the conduit in such a way that (a) the elution liquid is surrounded by the encapsulating liquid, (b) the sample liquid is flowed away from the trapping site, and (c) the elution liquid is flowed to the trapping site and surrounds the magnetic particles.

2. The system of claim 1 wherein the conduit is a capillary tube.

3. The system of claim 1 wherein the encapsulating liquid, sample liquid and elution liquid are flowed by negative pressure applied by the pump to the conduit.

4. The system of claim 1 wherein the encapsulating liquid, sample liquid and elution liquid are flowed by positive pressure applied by the pump to the conduit.

5. A system for handling a first sample liquid containing magnetic particles, a second sample liquid, and an encapsulating liquid, both sample liquids being immiscible with the encapsulating liquid, wherein the system is configured to perform a method comprising:
(a) flowing the encapsulating liquid in a conduit;
(b) flowing the first sample liquid containing magnetic particles in the conduit so that the first sample liquid is (i) surrounded by the encapsulating liquid and (ii) located at a predetermined trapping site within the conduit;
(c) immobilizing the magnetic particles of the first sample liquid at the trapping site by applying a magnetic field at the trapping site;
(d) flowing the first sample liquid in the conduit so that the first sample liquid is flowed away from the trapping site while the magnetic particles remain immobilized at the trapping site; and
(e) flowing the second sample liquid in the conduit so that the second sample liquid is (i) surrounded by the encapsulating liquid and (ii) surrounds the immobilized magnetic particles.

6. The system of claim 5, wherein the second sample liquid contains target biomolecules that bind to the magnetic particles when the second sample liquid surrounds the immobilized magnetic particles.

7. The system of claim 5, wherein the method further comprises, after flowing the second sample liquid, flowing an elution liquid in the conduit so that (a) the elution liquid is surrounded by the encapsulating liquid, (b) the second sample liquid is flowed away from the trapping site, and (c) the elution liquid is flowed to the trapping site and surrounds the immobilized magnetic particles.

8. The system of claim 7, wherein flowing the elution liquid further comprises freeing the target biomolecules from the magnetic particles by surrounding the magnetic particles with the elution liquid.

9. The system of claim 7, wherein the method further comprises mobilizing the magnetic particles in the elution liquid by removing the magnetic field after flowing the elution liquid.

10. The system of claim 7, wherein the elution liquid comprises a buffer.

11. The system of claim 5, wherein the method further comprises:
after flowing the second sample liquid, flowing a first cleaning liquid in the conduit so that (a) the first cleaning liquid is surrounded by the encapsulating liquid, (b) the second sample liquid is flowed away from the trapping site, and (c) the first cleaning liquid is flowed to the trapping site and surrounds the immobilized magnetic particles; and
after flowing the first cleaning liquid, flowing an elution liquid in the conduit so that (a) the elution liquid is surrounded by the encapsulating liquid, (b) the first cleaning liquid is flowed away from the trapping site, and (c) the elution liquid is flowed to the trapping site and surrounds the immobilized magnetic particles.

12. The system of claim 11, wherein the first cleaning liquid comprises ethanol.

13. The system of claim 5, wherein the method further comprises mobilizing the magnetic particles in the second sample liquid by removing the magnetic field after flowing the second sample liquid.

14. The system of claim 5, wherein the second sample liquid and the encapsulating liquid constitute a composite liquid cell.

15. The system of claim 5, wherein the system is configured to detect whether a marker is present by optical or fluorescent interrogation of the trapping site.

16. The system of claim 5, wherein the immiscible fluid comprises an oil.

17. The system of claim 16, wherein the oil is silicone oil, perfluorocarbon oil or perfluoropolyether oil.

18. The system of claim 5, wherein the conduit is a capillary tube.

19. The system of claim 5, wherein the system comprises the first sample liquid containing magnetic particles, the second sample liquid, and the encapsulating liquid, both sample liquids being immiscible with the encapsulating liquid.

20. The system of claim 19, further comprising an elution liquid and a cleaning liquid.

* * * * *